United States Patent [19]

Oliver

[11] 4,123,659
[45] Oct. 31, 1978

[54] RADIOGRAPHY

[75] Inventor: Colin C. Oliver, Slough, England

[73] Assignee: EMI Limited, Middlesex, England

[21] Appl. No.: 799,712

[22] Filed: May 23, 1977

[30] Foreign Application Priority Data

Jun. 1, 1976 [GB] United Kingdom ............... 22637/76

[51] Int. Cl.² ............................................. H05G 1/30
[52] U.S. Cl. ................................... 250/403; 250/355; 250/445 T
[58] Field of Search ............... 250/401, 402, 403, 404, 250/405, 445 T, 397, 398, 355

[56] References Cited

U.S. PATENT DOCUMENTS

| | | | |
|---|---|---|---|
| 2,946,892 | 7/1960 | Bas Taymaz | 250/404 |
| 3,838,284 | 9/1974 | McIntyre | 250/397 |
| 4,039,807 | 8/1977 | Bull | 250/445 T |

Primary Examiner—Craig E. Church
Attorney, Agent, or Firm—Cooper, Dunham, Clark, Griffin & Moran

[57] ABSTRACT

In a radiographic apparatus in which a scanning X-ray tube is used it is desirable to properly relate the scanning of the X-ray origin with other scanning motions of the apparatus. In this arrangement a scan progress detector is inserted partly into the radiation to detect its scan motion. In one example it is a collimator block to provide a sinusoidal output as the scan progresses. Pulses derived from the sinusoid are compared with signals representing an ideal scan and the differences between them used to correct the source scan control.

13 Claims, 9 Drawing Figures

RADIOGRAPHY

This invention relates to a method of and apparatus for constructing a representation of the variation of absorption with position across a planar slice of a body with respect to penetrating radiation such as X-radiation.

A method of and apparatus for constructing such a representation is described in U.S. Pat. No. 3,778,614. According to one example given in that specification, a scanning movement is imparted to a suitable source of radiation and a detector to provide a measure of the absorption suffered by each of a plurality of beams of radiation passing through the body in the plane of the slice. A technique for processing the absorption measurement is also disclosed in the said specification.

Scanning techniques capable of obtaining the desired data more rapidly are disclosed in U.S. Pat. Nos. 3,946,234 and 3,937,963. An alternative processing method involving a form of convolution has also been described in U.S. Pat. No. 3,924,129.

Further scanning techniques, which are developments of that disclosed in the said U.S. Pat. No. 3,937,963 have been described in U.S. applications Ser. Nos. 630,779 and 733,941. In the arrangements described therein a source of a fan shaped distribution of radiation, lying in a substantially planar region of examination is rotated about an axis substantially perpendicular to the fan distribution to direct the radiation through the region of examination from many directions. A plurality of detectors are arranged to measure the absorption of the radiation along individual beam paths in the fan at different angular positions thereof. In order to irradiate the region at a sufficient number of orientations additional motions may be imposed on the fan of radiation. In the examples described in the said applications Ser. Nos. 630,779 and 733,941 there are used X-ray sources which incorporate an elongated anode providing the fan shaped beam from a substantially point source at which an electron beam strikes the anode. By scanning the electron beam along the anode the point of origin of the X-rays is also scanned so that a lateral motion of the fan is superimposed on the orbital motion. Desired orientations of the fan in relation to the body can thus be provided by suitable relationship between the said two motions.

The said application Ser. No. 733,941 describes an arrangement for suitably relating the two motions and it is an object of this invention to provide an alternative arrangement therefor.

According to the invention there is provided an apparatus for examining a slice of the body of a patient, the apparatus including: a source, of a fan-shaped distribution of radiation originating from an anode included in the source, arranged to project the radiation through the body; detector means arranged to detect the intensity of the radiation after passage through the body; means for scanning the origin of the radiation in relation to the anode; and monitoring means, including further detector means, arranged to sample the radiation between the source and the body to provide scan signals indicative of the progress of the scanning.

In order that the invention may be clearly understood and readily carried into effect an example thereof will now be described with reference to the accompanying drawings of which.

Figure 1:
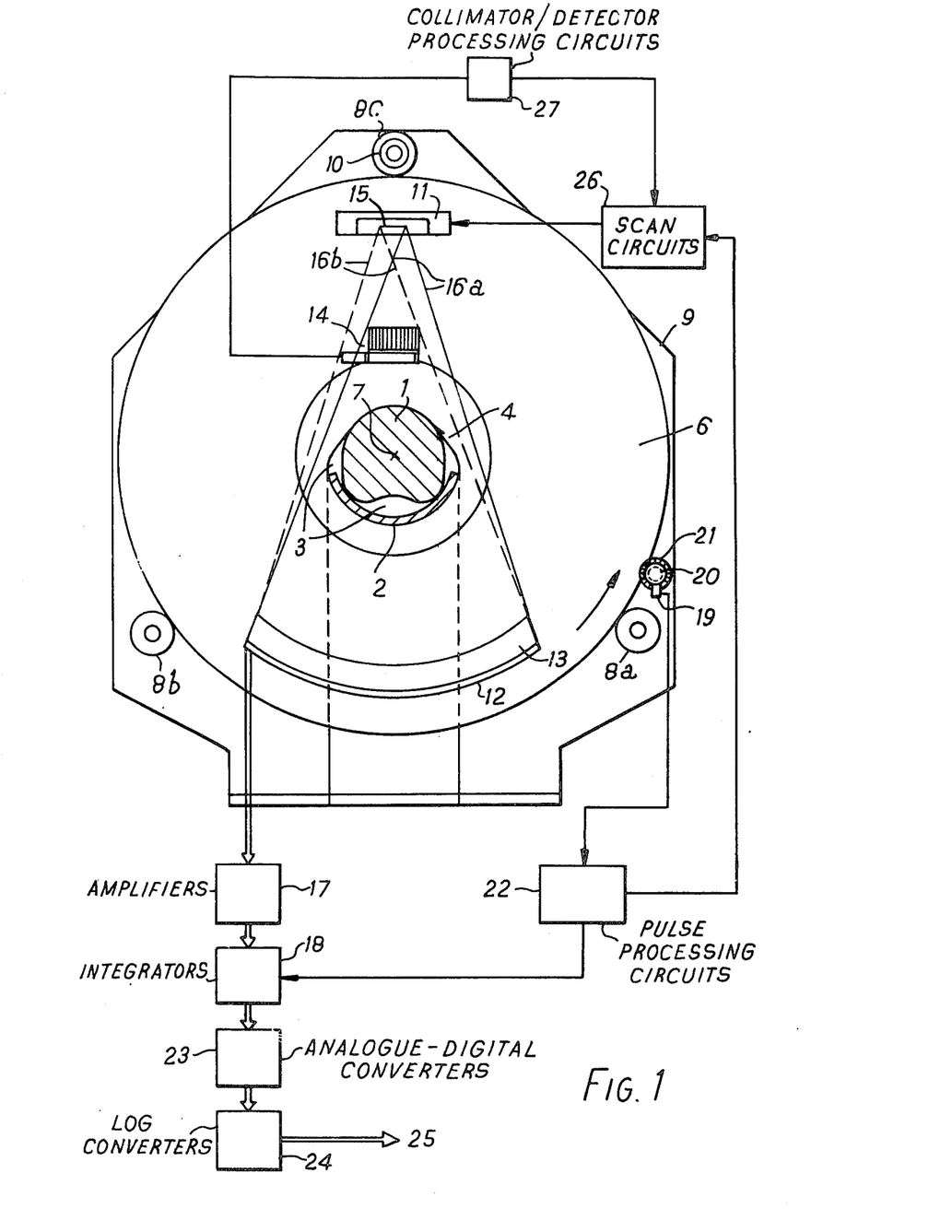
FIG. 1 shows an apparatus incorporating the invention.

Referring to FIG. 1, there is shown therein apparatus substantially the same as that described in the said application Ser. Nos. 733,941 and 630,779. A body 1 to be examined, shown in transverse section, is supported on a suitably shaped bed 2 also shown in transverse section. A material 3, having an absorption to the radiation similar to that of body tissue, is positioned between the body 1 and the bed 2, to substantially exclude air from gaps therebetween, and is extended partly about the body, to provide an approximately circular crosssection to the radiation. The body is retained firmly in the desired position by means such as a restraining strap 4.

The bed 2 and the body 1 are inserted into an aperture 5 in a rotatable member 6 so that a desired part of the body is centred in the aperture. The rotatable member 6 is arranged to rotated about an axis 7, in this example longitudinal to the body and perpendicular to the paper, central to the aperture 5. For that purpose it is supported by three gear wheels 8a, b, c, which engage with gear teeth, not shown, cut into the periphery of member 6. The gear wheels 8 are journalled in a main frame 9 of the apparatus. Gear wheel 8c is driven by a motor 10, also mounted on the main frame 9, to provide the necessary rotation.

The rotatable member 6 also carries a source 11 of x-rays, a bank of detectors 12 and associated collimators 13. The detectors, which in a typical embodiment number 300–400 can be of any suitable type, for example scintillation crystals with associated photomultipliers or photodiodes. A further collimator block and detector unit 14, which will be described in greater detail hereinafter, is also mounted on the main frame so as to be irradiated by the X-rays. In order to receive X-rays without shielding detectors 12, the unit 14 is displaced perpendicularly to the plane of examination i.e. perpendicular to the plane of the paper. The fan of X-rays is arranged to be at least of sufficient extend, perpendicular to the plane of the paper.

One or more wedge shaped attenuators, not shown, may also be included to tend to equalise the radiation path lengths across the substantially circular cross section of the body and packing material.

The source 11, which includes an elongated target/anode 15 as mentioned hereinbefore, provides a fan shaped spread 16, of X-rays from an area, which may be a point or a larger area such as a line, at which an electron beam is incident thereon. The electron beam can be scanned along the elongated anode to scan the X-rays correspondingly from the position 16a to the position 16b. This gives the effect of an extended source of X-rays although all of the radiation is not produced at one time. In this example the corresponding scan of the area which is the origin of the X-rays along target 15 is of the order of five cm. although it may be more or less if desired. The collimators have longitudinal axes which intersect in the region of the centre of anode 15.

Correspondingly the X-ray source 11 is placed of the order of 50cm from the central axis 7 with the detectors 12 being placed a further 50cm on the opposite side of axis 7 so as to intercept the radiation of fan 16 for any position of the origin of the X-rays in its lateral scan along target 15. If desired, however, the distances from source to axis 7 and detectors to axis 7 may be unequal. It should be understood that collimators 13 are of dimensions and construction which allow proper interception of the directly transmitted radiation while preventing the reception of scattered radiation to the greatest degree practically possible. Unit 14 may be placed closer to the source than shown provided it can intercept part of the radiation at all points of the scan without obscuring detectors 12.

The arrangement is such that the origin of the X-rays is scanned steadily along target 15 taking the fan of X-rays from 16a to 16b and is rapidly returned to the starting point before repeating the scan. Simultaneously the rotary member 6 and the equipment mounted thereon are subject to a required rotation. During this time each detector of array 12 is providing an output indicative of the intensity of radiation incident thereon. These outputs are amplified in amplifiers 17 and then input to integrators 18. There the outputs are integrated over periods chosen such that each integrated output is related to the intensity of radiation transmitted along a beam path, of dimensions determined by the rotational motion and source point linear motion in that period. Since these motions are related in a manner chosen to achieve desired beam paths for a particular embodiment, say that of application No. 630,779, the required periods of integration are also related to these motions. For this purpose the integrators are, in this example, set and reset by pulses of period related to the orbital motion. These are provided by a light source and photocell unit 19 mounted on main frame 9. Journalled in main frame 9 is a further gear wheel 20 engaging the teeth cut in the periphery of member 6. Carried on wheel 20 is a circular graticule 21 which thus rotates with member 6. The graticule 21 comprises opaque lines on a transparent substrate so that these lines interrupt a light path between the said light source and photocell to give pulses indicating the progress of the rotary motion. The pulses are applied to integrators 18 via a unit 22 which will be discussed hereinafter.

In this example the timing of the pulses is such that there are twenty four integration periods in the time of one lateral scan of the X-ray fan 16 from 16a to 16b. Thus each detector measures radiation in effect along twenty four narrow beam paths joining that detector with 24 equally spaced positions along target 15. The actual shape of the paths through the body will be, as mentioned hereinbefore, also determined by the simultaneous orbital motion. Signals representing the intensity of radiation received along those paths are converted to digital forms in converters 23 and to logarithmic form in convertors 24 for output at 25 for further processing. It will be understood that one amplifier 17, integrator 18, A/D converter 23 and log converter 24 is provided for every detector, all operated in synchronism. The processing is effective to sort the signals into sets representing absorption along sets of parallel paths, for example as explained in application Ser. No. 630,779, for processing by a suitable method such as that described in our U.S. Pat. No. 3,924,129 to provide the desired representation. The circuits referred to are of well known construction.

As mentioned hereinbefore it is desired to maintain the scanning of X-ray source 11 in a required relationship with the continuous rotary motion. For this purpose scan circuits 26, controlling the scanning of the incident electron beam along anode 15, are provided with the pulses from light source and photocell unit 19 via graticule pulse processing circuits 22. It is however also desirable to monitor the actual lateral motion of the X-rays to ensure that the relationship is properly achieved. An output for this purpose is provided by unit 14, via processing circuit 27 also to scan circuits 26.

Figure 2:
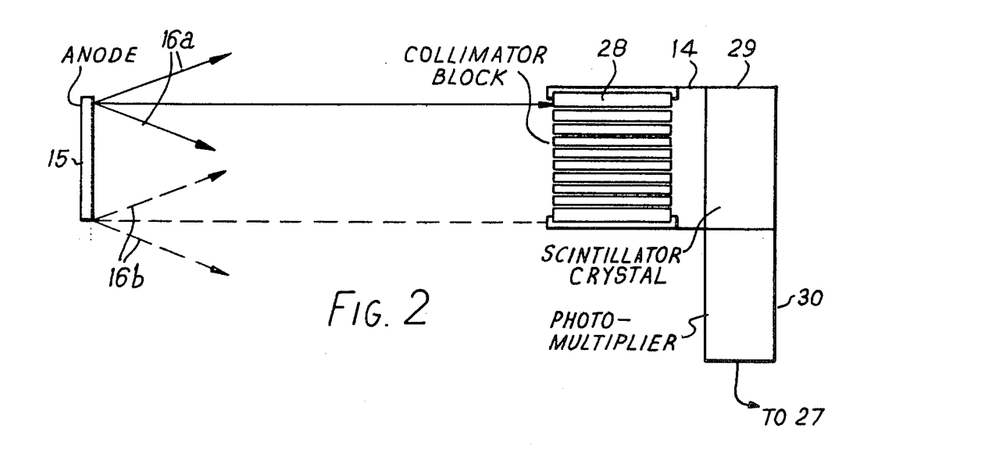
FIG. 2 shows a collimator detector arrangement for implementing the invention.

The arrangement of the collimator detector unit 14 is shown in greater detail in FIG. 2. The fan of X-rays can be scanned from 16a to 16b as the origin thereof moves, in this example, five cm along anode 15. Disposed slightly out of the plane of examination, unit 14 comprises a collimator block 28, in this example 25 cm, at its mid point from anode 15, allowing substantially only radiation in a predetermined angle in the fan, in this example perpendicular to the anode, to irradiate a scintillator crystal 29. The intensity of light emitted by scintillator 29, in response to incident radiation, is measured by a detector 30 which can be a photomultiplier or other suitable device. Alternatively scintillator 29 can be replaced with an alternative detector such as a xenon filled proportional counter.

Collimator block 28 is formed from a plurality of blocks of X-rays absorbing material, such as lead or brass, and in a typical example, suitable to a distance of 25cm from the anode, provides 0.15mm apertures, to the radiation, at 2.5mm pitch over, say, a total length of 5cm. For clarity, however, FIG. 2 shows an example of larger relative proportions. It will be understood that if the block 28 is placed at a different distance from the X-ray source (another typical example is placed at 13.5cm) the relative proportions may be changed. Means, not shown, are also provided to displace the collimator block laterally and/or angularly in relation to the anode 15 for the purposes of initial adjustment. The collimator block is adjusted so that when scintillator 29 receives radiation through one aperture its receives little radiation through adjacent apertures. Thus, as the X-ray fan 16 is scanned laterally, the light output of the scintillator 29 and hence the output of multiplier 30 rises and falls as the X-rays pass across successive collimator apertures. In practice the X-ray intensity from the area of origin has a Gaussian distribution across that area. For this reason the output of unit 14 in the course of a scan is an approximate sinusoid as shown in FIG. 3a.

It will be understood that, if this output is to be used for timing procedures, a sinusoid is not a convenient form. It is therefore, after filtering to reduce noise, applied to an edge detection circuit. Such circuits may be devised to provide a pulse indicating the detection of a leading edge, as in FIG. 3b, or a trailing edge. Alternatively a more complex circuit may be provided to detect the leading and trailing edges and to provide pulses, with a suitable delay, indicative of the relative timing of the peaks midway between the two edges. Such pulses would move closely indicate the presence of the centre of the x-ray origin.

Figure 4:
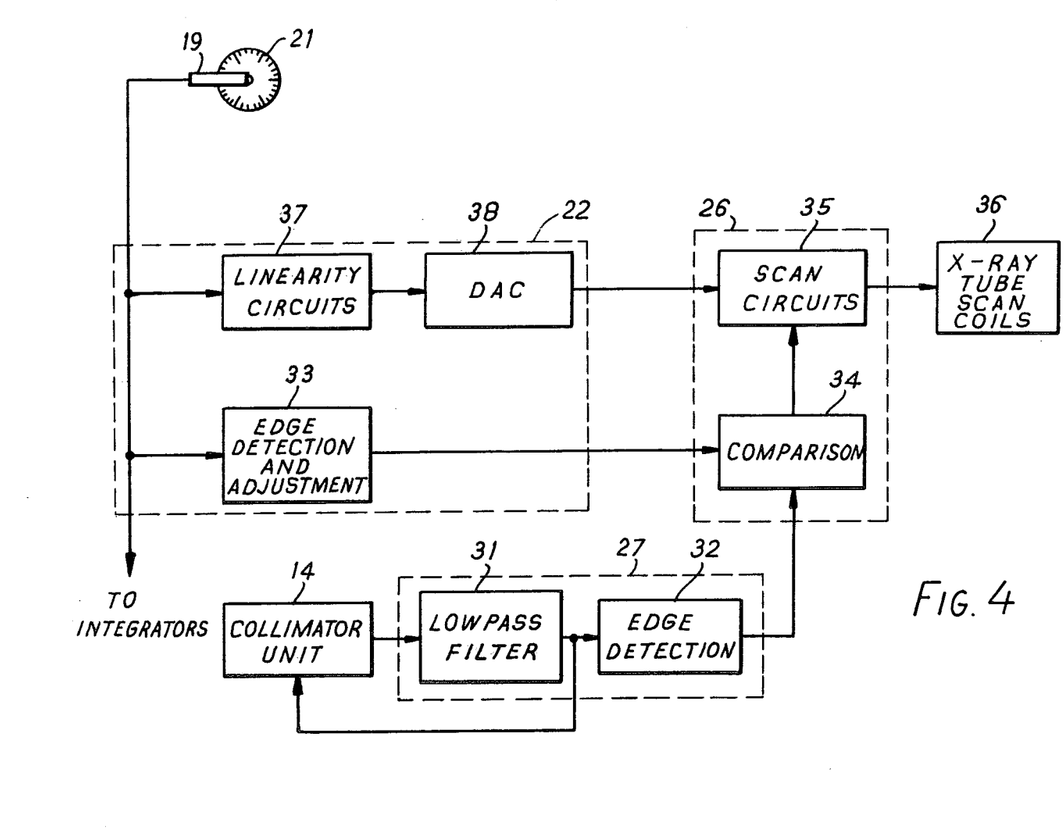
FIG. 4 is a block diagrammatic circuit for processing the control signals for the apparatus of FIG. 1.

A block diagram of the timing circuits is shown in FIG. 4. The output of the photomultiplier in unit 14 is processed as described by a low pass filter 31 and edge detection circuit 32, together constituting circuits 27, to give pulses indicative of the progress of the x-ray scan. The overall amplitude of the output, from low pass filter 31 may be fed back to the photomultiplier as a gain control for stabilisation purposes.

Figure 3:
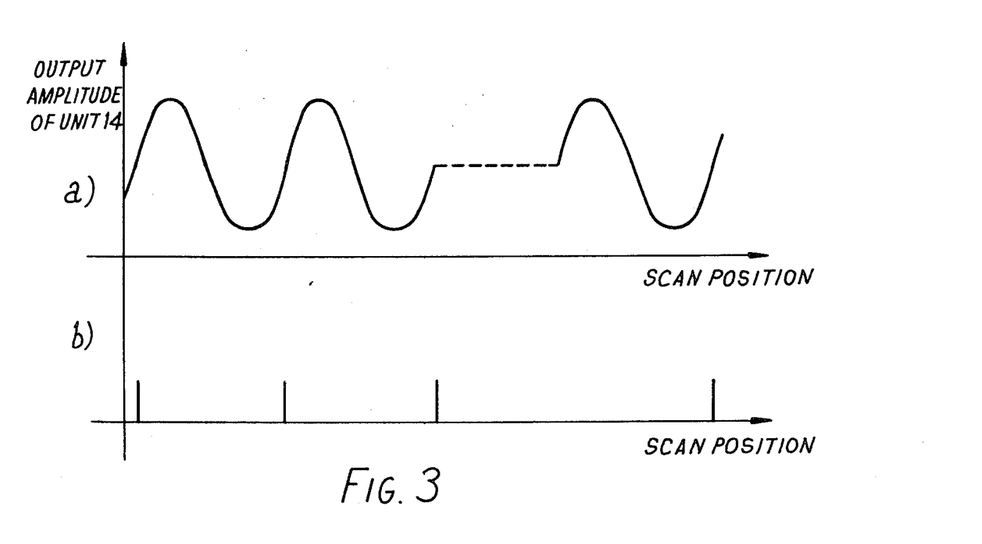
FIG. 3 illustrates the form of the output of the arrangement of FIG. 2.

The photocell unit 19 associated with graticule 21 provides timing pulses indicating the integration intervals referred to hereinbefore and scan timing pulses indicating the correct times, for a desired scan relationship, of the pulses, such as those of FIG. 3b, which represent a chosen characteristic of the output of unit 14. These two sets of pulses may be identical, if the relationship is suitable, or may be independent, but of related timing. In the latter case they can be provided by two photocells detecting lines of different graticules on wheel 20.

The graticule scan timing pulses are provided to edge detection circuits 33 which provide pulses of suitable form for comparison and also allow fine adjustment of their relative timing for use in initially setting up the apparatus. The pulses are then compared in circuits 34 with the actual scan pulses derived from unit 14. Any errors of timing between the two are applied to X-ray scan circuits 35 which control the X-ray tube scanning coils, indicated generally at 36, to correct the X-ray scan timing. Circuits 34 and 35 constitute the circuits 26 referred to hereinbefore.

The initial scan sawtooth, prior to adjustment in circuits 35, may be preset. However in a preferred embodiment the sawtooth is derived from the pulses provided by photocell unit 19. These are used by linearity circuits 37, which may be digital, to provide a sawtooth which is approximately related to the rotation rate, scan circuits 35 then provide a fine adjustment. If circuits 37 are digital their output is in the form of a pulse train which is applied to a digital to analogue converter (DAC) 38 to give the actual sawtooth.

Figure 5:
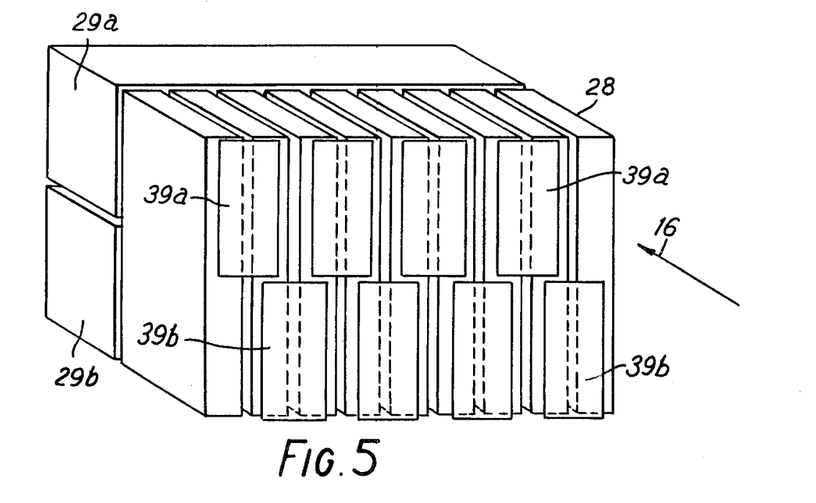
FIG. 5 shows an alternative collimator detector arrangement.

An alternative form of the collimator block 14, capable of providing a greater amplitude of output for a closer aperture pitch, is shown in FIG. 5. The collimators 28 are extended in a direction perpendicular to the X-ray fan and the unit is provided with two scintillators 29a and 29b and associated photomultipliers (not shown). At one end of the collimator apertures, through which radiation is admitted to scintillator 29a, alternate apertures are obscured by lead plates 39a. At the opposite end, through which radiation is admitted to 29b, the intervening apertures are obscured by lead plates 39b. The effect is that each scintillator receives radiation through alternate apertures, those for the two scintillators being interleaved.

Figure 6:
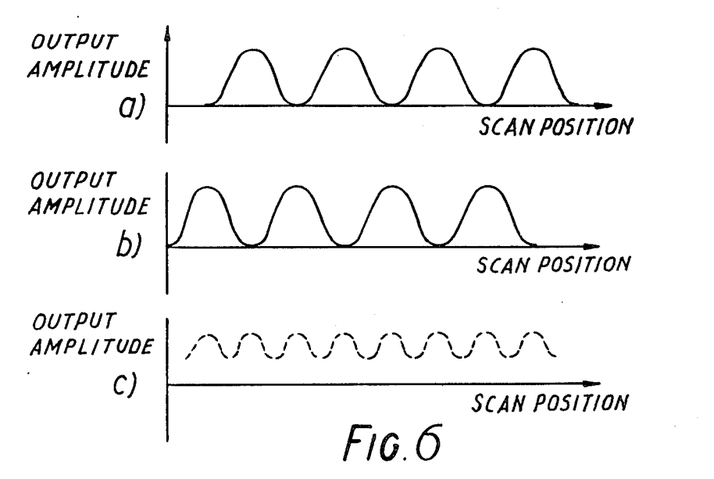
FIG. 6 shows the form of the output of the FIG. 5 arrangement.

Thus as the source of the radiation is scanned, from left to right of FIG. 5, the outputs of the photomultipliers associated with scintillators 29a and 29b are as shown in FIG. 6a and 6b respectively. FIGS. 5 and 6 are aligned to show the apertures of block 14 to which each peak relates. It will be seen that if the pitch of the collimator apertures is halved each of FIG. 6a and 6b will be of substantially the same amplitude as that of FIG. 3a. The sinusoidal outputs are subject to independent edge detection and then combined so that double the frequency of timing pulses is provided, without loss of accuracy.

If the aperture pitch is halved without using the expedient of FIG. 5 the output would be as in FIG. 6c which has twice the frequency at half the amplitude and which will lose accuracy in the placing of the timing pulses to be derived from it.

In FIG. 5 the lead plates are shown before the collimators 28, for clarity or explanation. Preferably they should be placed between the collimator block and the scintillators. Alternatively the respective parts of the apertures can be filled with radiation absorbent material.

The collimator block 14 of FIG. 5 must be inserted to a greater extent into the radiation. It can be divided into two parts (a and b) inserted into the radiation on opposite sides to that which is to pass through the patient and inserted to the same extent as that of FIG. 2. However care must be taken that the two sides are properly aligned and maintained in a correct relationship.

It will be understood that other circuits may be devised to control the X-ray scan from the output of unit 14. These may be arranged to obtain timing from any repeating characteristic of the waveform of FIG. 3a or a similar waveform resulting from an alternative form of unit 14. Alternatively the timing signals may be used to control the rotation to keep time with the X-ray scan instead of the reverse. Furthermore the single detector providing outputs for different scan positions, as a result of the provision of well defined collimator appertures, may be replaced by a plurality of individual detectors, such as photodiodes, spaced across the X-ray scan. Other arrangments which are equivalent to collimators, such as aligned apertures of two or more gratings, may be used or any other arrangement giving a modulated output indicative of the X-ray scan. Furthermore it will be realised that the collimator apertures, or similar means, need not be parallel to each other but can be disposed at other orientations, for example in a fan distribution, provided they transmit radiation from the source thoughout its scan and that the geometry is accurately known.

Figure 7:
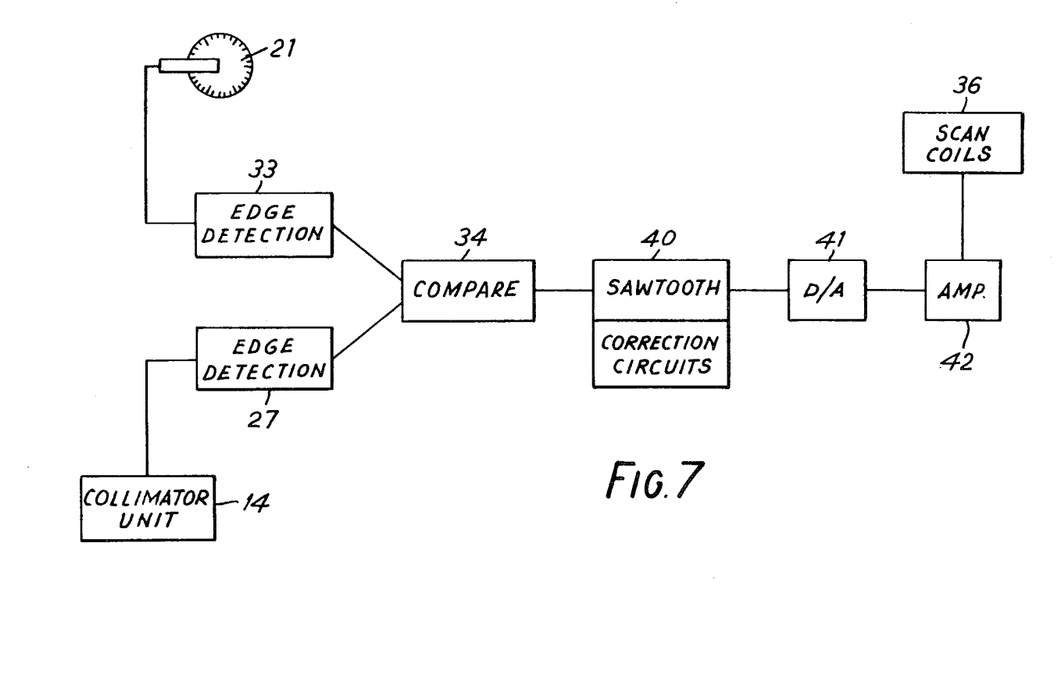
FIG. 7 shows an alternative circuit to that of FIG. 4.

FIG. 7 shows an laternative circuit to that of FIG. 4. The circuit of FIG. 7 takes the pulses derived from the collimator unit 14 by edge detector 27 and compares them directly in a unit 34 with the timing signal from graticule 21.

Signals representing the timing differences resulting from the comparison are applied to a unit 40 which provides an adjusted sawtooth output. This sawtooth is continuously adjusted, in practice over discrete small sections, to provide a sawtooth tending to cause the scan to conform to the timing signals. The sawtooth is in practice produced in digital form, in which case it must be converted into analogue form in a converter 41. It is then amplified in a drive amplifier 42 and applied to the scan coils 36.

Figure 8:
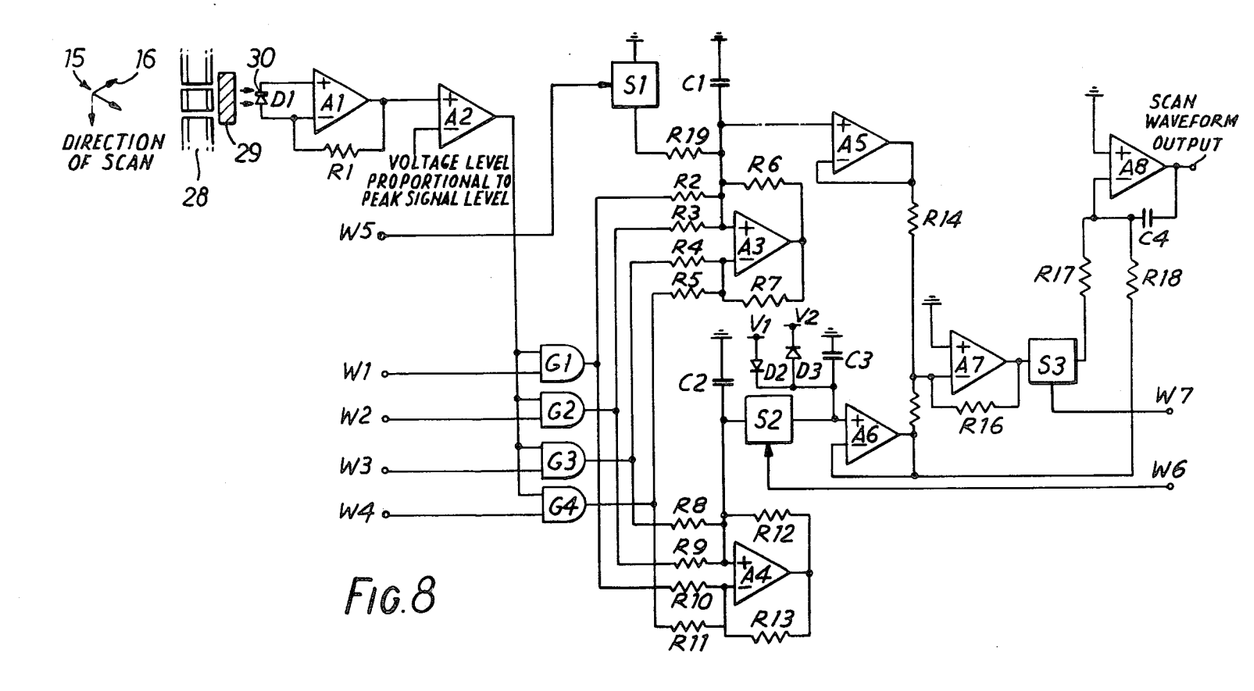
FIG. 8 shows a further alternative circuit and FIG. 9 is a timing diagram used to explain FIG. 8.

A further alternative circuit, shown in FIG. 8 is suitable for use with a collimator unit 28 having two apertures, to adjust the amplitude and relative shift of the X-ray source spot scan. It is assumed in this circuit that a linear scan is provided since non-linearities can, if present, be adequately removed by known fixed correction networks. The circuit can be adapted to collimator units with more slots, but as shown two are provided, one to produce a pulse after approximately 20% of the scan and another to produce a pulse after approimately 80% of the scan. It is assumed that a relatively rapid flyback scan takes place (approximately 3x the spead of the forward scan) and that a grid pulse blanks out the X-rays during the flyback.

The forward scan crossing the collimator slits causes two bursts of light from the scintillator 29 and two subsequent peaks of current in the detector, in this case a photodiode D1. This current is amplified in an amplifier A1 and squared off by a comparator A2. The reference voltage for the comparison is arranged to be proportional to the peak signal voltage at the other input (in this example being one half of that voltage).

Figure 9:
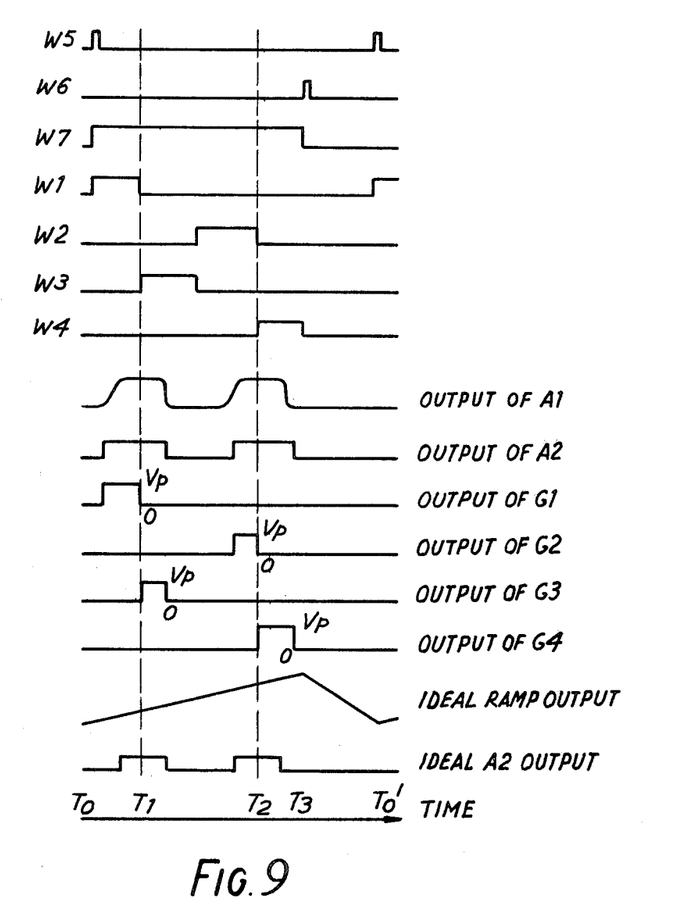

In FIG. 9 there is shown a timing diagram which will be referred to in describing FIG. 8. On the time scale there are shown times $T_o$ and $T_3$ which represent the start and end of the desired scan as provided by an ideal ramp. Times $T_1$ and $T_2$ represent the times at which the collimator unit output pulses should occur for an ideal scan. Time $T_o'$ is the start of the next scan. $T_o$ to $T_3$ may be set ideally but are preferably provided by pulses derived from graticule unit 21. The times $T_1$ and $T_2$ are also shown by the broken lines on all the other waveforms.

Waveforms $W_1$ - $W_7$ are timing waveforms provided by circuits which are well known in the circuit art and which have therefore not been shown. It can be seen that $W_1$ to $W_4$ are equal size positive going pulses to one side or the other of times $T_1$ and $T_2$ so that the falling edge of $W_1$ and the rising edge of $W_3$ occur at time $T_1$, and the falling edge of $W_2$ and the rising edge of $W_4$ occur at time $T_2$.

$W_5$ is a scan start pulse at $T_o$, $T_o'$ etc and $W_6$ is a scan stop pulse (flyback pulse) at $T_3$ etc. $W_7$ is a gate waveform which has a positive value between $T_o$ and $T_3$. This can also control the X-ray blanking during flyback. The other waveforms shown are those found at marked points in the circuit. Returning to FIG. 8, an and gate $G_1$ passes only that part of the squared-off input waveform which occurs prior to $T_1$. Similarly a gate $G_3$ passes only that part which occurs after $T_1$. If these waveforms are integrated and subtracted, the resulting voltage is a measure of the timing error of the original pulse's centre point relative to $T_1$. It can be seen from the example shown in FIG. 9 that the first pulse is not centred on $T_1$ so that the pulse at the output of $G_1$ has a greater duration than that at the output of G3. Two similar gates $G_2$ and $G_4$ divide the second pulse in a similar manner at time $T_2$.

An Amplifier $A_4$, with resistors $R_8$ - $R_{13}$ is arranged in a current generation configuration. The outputs of $G_1$ and $G_4$ causes a constant negative current to flow into a capacitor $C_2$. A positive current flow is provided into $C_2$ by outputs on gates $G_2$ and $G_3$. In the case when $G_1$ $t$ $G_4$ equals $G_2$ $t$ $G_3$, in terms of total pulse width, the net current into $C_2$ is zero. In that case the amplitude of the scan is deemed to be correct and no change in the scan current is called for. If the pulses of $G_1$ and $G_4$ are wider in total than those of $G_2$ and $G_3$ then the scan is proceeding too slowly and the scan current should be increased. The change on $C_2$ is arranged to become more negative in that case. At the end of the scan a gate $S_2$ is opened and $C_2$ is connected to a further capacitor $C_3$. The voltage on $C_3$ is buffered by an amplifier $A_6$ and integrated at $A_8$, $C_4$ and $R_{18}$ to provide the desired scan waveform. It can be seen that $S_2$ is opened at the end of each scan to set $C_3$ for the next scan in the light of errors in the previous one. An initial value is set on $C_3$ for first scan and the voltage on $C_3$ is kept within desired limits by diodes $D_2$ and $D_3$ and voltage levels $V_1$ and $V_2$.

Flyback occurs when a switch $S_3$ is closed by waveform $W_7$. The inverting amplifier $A_7$ feeds an additional current of, say, $-4X$ the forward scan current, into the integrator; resulting in an inversion of the output ramp and an increase of slope of $(4-1)X$, i.e. 3X for the flyback.

Shift errors are corrected during flyback. The shift error is represented by the net time error of $G_1 + G_3 - (G_2 + G_4)$. The integrator is an amplifier $A_3$ and resistors $R_2$ to $R_7$ with Capacitor $C_1$. A voltage follower $A_5$ passes the resultant error into the virtual earth amplifier $A_7$ where it is added to the normal flyback control.

After each flyback period a switch 51 closes and passes a large part of the charge on $C_1$ ground, leaving a proportion of the previous correction voltage on $C_1$ to be added to the correction for the next cycle. This arrangement provides greater smoothness of control by spreading out each correction over more than one cycle.

It should be noted that, for both amplitude and shift corrections, only small corrections are made for any one cycle so that full correction requires approximately 10 cycles. This helps to prevent the occurrence of oscillating errors.

The circuit of FIG. 8 may be implemented in any suitable manner. It may be noted, however, that the following circuits have been found to be suitable for this purpose: for amplifier $A_1$ the LF 357 circuit of National Semiconductor; for amplifier $A_2$ the CA 3130 circuit of RCA; for amplifiers A3–A8, the LF 356 circuit of National Semiconductor; for gates G1–G4 the CD 4081B circuit of RCA; and for switches 51-53, the CD 4066 Quad Tx Gate of RCA. It has also been found that the efficient operation it is desirable for resistors $R_2$ - $R_5$ and $R_6$ - $R_{11}$ to be equal and for $R_6$ to equal $R_7$, $R_{12}$ to equal $R_{13}$, $R_{16}$ to equal $4R_{15}$ and $R_{17}$ to equal $R_{18}$.

Although in the arrangement described the scan monitor signals are used to adjust the X-ray scan, they may be retained in storage and used to correct the final data for errors caused by scan inaccuracies.

In certain arrangements the entire rotation of the X-ray fan may be by electronic scanning of an extended source. In that case one or more scan monitoring means as described may be used to monitor the outline scanning motion.

In other variations of the described apparatus the scan of the X-ray origin relative to the source may be provided by a rotating anode of appropriate shape to move the point of impact of the electron beam, as described in U.S. application Ser. No. 733,220.

What I claim is:

1. An apparatus, for examining a region of the body of a patient by means of penetrating radiation, including a source of radiation arranged to project the radiation from an origin in the source along a plurality of paths through the body, means for displacing the origin of the radiation relative to the source to project the radiation through the body along different paths, detector means disposed to receive the radiation emerging from the body after traversing said paths, monitoring means, disposed between the source and the body, for detecting part of the radiation emitted from the source during said displacement to provide scan signals indicative of the progress of said displacement and means for comparing the scan signals with control signals, indicative of a desired progress of said displacement, to tend to reduce variations of said indicated progress from said desired progress.

2. An apparatus according to claim 1 in which the means for comparing includes means arranged to provide error signals indicative of timing differences between the scan signals and the control signals and the means for scanning includes means responsive to the error signals to reduce said variations.

3. An apparatus according to claim 1 in which the monitoring means includes means disposed to modulate the intensity of the radiation incident thereon in a manner related to the position of said origin in its displacement and further detector means for detecting the intensity of the modulated radiation.

4. An apparatus according to claim 3 in which the means disposed to modulate the radiation includes means disposed to selectively admit to the further detector means radiation emitted from a plurality of spaced positions of said displacement.

5. An apparatus according to claim 4 in which the means disposed to modulate includes collimator means having a plurality of apertures for admitting radiation to the further detector means.

6. An apparatus according to claim 5 in which the collimator apertures are substantially parallel and perpendicular to the locus of said displacement.

7. An apparatus according to claim 5 in which the collimator means has two sets of apertures having related spacing and the further detector means is two detectors each receiving radiation admitted by one of said sets of apertures.

8. An apparatus according to claim 7 in which the collimator means is a single collimator block of which alternate apertures are obscured for radiation which would be incident on one detector and the other apertures are obscured for radiation which would be incident on the other detector.

9. An apparatus according to claim 7 in which the collimator means is disposed with one set of apertures to one side of the radiation which will pass through the body and the other set of apertures are disposed to the other side thereof.

10. An apparatus according to claim 1 in which the monitoring means includes a plurality of detectors and means for combining the outputs of the detectors, or signals related thereto, to provide the scan signals.

11. Radiographic apparatus for examining a slice of the body of a patient, the apparatus including a source of a substantially planar fan-shaped distribution of radiation originating from an anode included in the source, means for scanning the origin of the radiation in relation to the anode and a scan position indicator which includes means for detecting the intensity of part of the radiation prior to traversing the body and means disposed to modulate the intensity of the radiation incident on the means for detecting in a manner related to the position of said origin in its scan.

12. An apparatus for examining a slice of the body of a patient, the apparatus including: a source, of a fan-shaped distribution of radiation originating from an anode included in the source, arranged to project the radiation through the body; detector means arranged to detect the intensity of the radiation after passage through the body; means for scanning the origin of the radiation in relation to the anode; and monitoring means, including further detector means, arranged to sample the radiation between the source and the body to provide scan signals indicative of the progress of the scanning.

13. An apparatus for examining a region of the body of a patient by means of penetrating radiation, the apparatus including: means defining a patient position and source means including an anode disposed outside the patient position for generating a substantially planar fan-shaped distribution of radiation originating substantially from an area of said anode; a plurality of detectors for detecting the radiation after passage through the patient position along a plurality of beam paths at different angles within the fan-shaped distribution; means for displacing the source means relative to the patient position to direct the radiation along beam paths disposed at different orientations in the region; means for additionally subjecting the origin of the radiation to a periodic displacement relative to said anode to irradiate the patient position along further beam paths; means, disposed between the source means and the patient position for sampling the radiation emitted from said anode during said periodic displacement to provide signals indicative of the progress of said periodic displacement; means for generating control signals, indicative of a desired progress of said periodic displacement; means for comparing the scan signals with the control signals to produce error signals indicative of variations between the indicated progress and the desired progress; and means, operating in response to the error signals, to control the progress of the scan to tend to reduce said variations.

* * * * *